US009199067B2

(12) United States Patent
Heilman et al.

(10) Patent No.: US 9,199,067 B2
(45) Date of Patent: Dec. 1, 2015

(54) ENDOVASCULAR CEREBROSPINAL FLUID SHUNT

(71) Applicant: Tufts Medical Center, Inc., Boston, MA (US)

(72) Inventors: Carl Heilman, Wayland, MA (US); Adel M. Malek, Weston, MA (US)

(73) Assignee: Tufts Medical Center, Inc., Boston, MA (US)

( * ) Notice: Subject to any disclaimer, the term of this patent is extended or adjusted under 35 U.S.C. 154(b) by 0 days.

(21) Appl. No.: 14/179,622

(22) Filed: Feb. 13, 2014

(65) Prior Publication Data

US 2014/0336559 A1 Nov. 13, 2014

Related U.S. Application Data

(60) Continuation of application No. 13/569,212, filed on Aug. 8, 2012, now Pat. No. 8,672,871, which is a division of application No. 12/362,152, filed on Jan. 29, 2009, now abandoned.

(51) Int. Cl.
*A61M 27/00* (2006.01)
*A61M 39/22* (2006.01)
(Continued)

(52) U.S. Cl.
CPC .......... *A61M 27/006* (2013.01); *A61M 25/0075* (2013.01); *A61M 27/002* (2013.01); *A61F 2230/0091* (2013.01); *A61M 2025/0076* (2013.01); *A61M 2202/0464* (2013.01);
(Continued)

(58) Field of Classification Search
CPC ............ A61M 27/006; A61M 27/002; A61M 2025/0076; A61M 25/0075; A61M 2210/0612; A61M 2210/0662; A61M 2210/0668; A61M 2210/0675; A61M 2210/0681; A61M 2210/0687; A61M 2210/0693; A61M 2202/0464; A61M 2025/0078; A61F 9/00781; A61F 9/0017; A61F 11/002; A61F 2002/30289; A61F 2230/0091
See application file for complete search history.

(56) References Cited

U.S. PATENT DOCUMENTS 3,492,996 A 2/1970 Fountain
4,413,985 A 11/1983 Wellner et al.
(Continued)

FOREIGN PATENT DOCUMENTS

EP 0964636 12/1999
EP 1047341 11/2000
(Continued)

OTHER PUBLICATIONS

PCT International Search Report and Written Opinion for International Application No. PCT/2015/011317, Applicant Tufts Medical Center Inc., Forms PCT/ISA/210, 220, and 237, dated Mar. 26, 2015 (15 pages).
(Continued)

*Primary Examiner* — Adam Marcetich
(74) *Attorney, Agent, or Firm* — Occhiutti & Rohlicek LLP

(57) ABSTRACT

An endovascular implantable shunt device for draining cerebrospinal fluid from a patient's subarachnoid space includes a shunt having opposed first and second ends, a one-way valve is located at the first end of the shunt, a helical tip is disposed at the second end, and a hollow passageway extends between the helical tip and one-way valve. The helical tip is constructed to penetrate a patient's sinus wall. Cerebrospinal fluid drains through the helical tip and out through the valve.

10 Claims, 5 Drawing Sheets

(51) Int. Cl.
*A61M 39/24* (2006.01)
*A61M 25/00* (2006.01)

(52) U.S. Cl.
CPC ............... *A61M2210/0687* (2013.01); *A61M 2210/0693* (2013.01)

(56) References Cited

U.S. PATENT DOCUMENTS

| | | | |
|---|---|---|---|
| 4,474,569 A | 10/1984 | Newkirk | |
| 4,475,898 A | 10/1984 | Brodner et al. | |
| 4,631,051 A | 12/1986 | Harris | |
| 4,737,153 A | 4/1988 | Shimamura et al. | |
| 4,950,232 A | 8/1990 | Ruzicka et al. | |
| 5,000,731 A | 3/1991 | Wong et al. | |
| 5,193,546 A | 3/1993 | Shaknovich | |
| 5,385,541 A | 1/1995 | Kirsch et al. | |
| 5,405,316 A | 4/1995 | Magram | |
| 5,496,329 A * | 3/1996 | Reisinger | 606/109 |
| 5,551,427 A * | 9/1996 | Altman | 600/374 |
| 5,746,725 A * | 5/1998 | Shalon et al. | 604/246 |
| 5,830,222 A | 11/1998 | Makower | |
| 5,851,199 A | 12/1998 | Peerless et al. | |
| 6,015,405 A | 1/2000 | Schwartz | |
| 6,068,638 A | 5/2000 | Makower | |
| 6,071,292 A | 6/2000 | Makower et al. | |
| 6,126,628 A | 10/2000 | Nissels | |
| 6,126,649 A | 10/2000 | Van Tassel et al. | |
| 6,159,225 A | 12/2000 | Makower | |
| 6,186,972 B1 | 2/2001 | Nelson et al. | |
| 6,190,353 B1 | 2/2001 | Makower et al. | |
| 6,231,587 B1 | 5/2001 | Makower | |
| 6,283,934 B1 | 9/2001 | Borgesen | |
| 6,283,951 B1 | 9/2001 | Flaherty et al. | |
| 6,283,983 B1 | 9/2001 | Makower et al. | |
| 6,287,317 B1 | 9/2001 | Makower et al. | |
| 6,302,875 B1 | 10/2001 | Makower et al. | |
| 6,330,884 B1 | 12/2001 | Kim | |
| 6,375,615 B1 | 4/2002 | Flaherty et al. | |
| 6,379,319 B1 | 4/2002 | Garibotto et al. | |
| 6,432,127 B1 | 8/2002 | Kim et al. | |
| 6,491,707 B2 | 12/2002 | Makower et al. | |
| 6,508,824 B1 | 1/2003 | Flaherty et al. | |
| 6,544,230 B1 | 4/2003 | Flaherty et al. | |
| 6,561,998 B1 | 5/2003 | Roth et al. | |
| 6,569,145 B1 | 5/2003 | Shmulewitz et al. | |
| 6,579,311 B1 | 6/2003 | Makower | |
| 6,589,164 B1 | 7/2003 | Flaherty | |
| 6,602,241 B2 | 8/2003 | Makower et al. | |
| 6,613,081 B2 | 9/2003 | Kim et al. | |
| 6,616,675 B1 | 9/2003 | Evard et al. | |
| 6,638,293 B1 | 10/2003 | Makower et al. | |
| 6,655,386 B1 | 12/2003 | Makower et al. | |
| 6,660,024 B1 | 12/2003 | Flaherty et al. | |
| 6,685,648 B2 | 2/2004 | Flaherty et al. | |
| 6,685,716 B1 | 2/2004 | Flaherty et al. | |
| 6,709,444 B1 | 3/2004 | Makower | |
| 6,719,750 B2 * | 4/2004 | Varner et al. | 604/289 |
| 6,726,677 B1 | 4/2004 | Flaherty et al. | |
| 6,746,426 B1 | 6/2004 | Flaherty et al. | |
| 6,746,464 B1 | 6/2004 | Makower | |
| 6,863,684 B2 | 3/2005 | Kim et al. | |
| 7,056,325 B1 | 6/2006 | Makower et al. | |
| 7,083,588 B1 | 8/2006 | Shmulewitz et al. | |
| 7,094,230 B2 | 8/2006 | Flaherty et al. | |
| 7,134,438 B2 | 11/2006 | Makower et al. | |
| 7,179,270 B2 | 2/2007 | Makower et al. | |
| 7,191,015 B2 | 3/2007 | Lamson et al. | |
| 7,303,571 B2 | 12/2007 | Makower et al. | |
| 7,316,655 B2 | 1/2008 | Garibotto | |
| 7,357,794 B2 | 4/2008 | Makower et al. | |
| 7,407,506 B2 | 8/2008 | Makower et al. | |
| 7,606,615 B2 | 10/2009 | Makower et al. | |
| 7,637,870 B2 | 12/2009 | Flaherty et al. | |
| 7,648,517 B2 | 1/2010 | Makower et al. | |
| 7,670,329 B2 | 3/2010 | Flaherty et al. | |
| 7,729,738 B2 | 6/2010 | Flaherty et al. | |
| 7,846,172 B2 | 12/2010 | Makower | |
| 7,955,343 B2 | 6/2011 | Makower et al. | |
| 7,966,057 B2 | 6/2011 | Macaulay et al. | |
| 8,075,580 B2 | 12/2011 | Makower et al. | |
| 8,083,708 B2 | 12/2011 | Flaherty et al. | |
| 8,090,430 B2 | 1/2012 | Makower et al. | |
| 8,214,015 B2 | 7/2012 | Macaulay et al. | |
| 8,295,947 B2 | 10/2012 | Lamson et al. | |
| 8,585,596 B1 | 11/2013 | Flaherty et al. | |
| 8,672,871 B2 | 3/2014 | Heilman et al. | |
| 8,672,920 B2 | 3/2014 | Makower et al. | |
| 8,727,988 B2 | 5/2014 | Flaherty et al. | |
| 8,753,366 B2 | 6/2014 | Makower et al. | |
| 2002/0188308 A1 | 12/2002 | Tu et al. | |
| 2003/0135147 A1 | 7/2003 | Rosenberg et al. | |
| 2003/0181938 A1 | 9/2003 | Roth et al. | |
| 2003/0220604 A1 | 11/2003 | Al-Anazi | |
| 2003/0229366 A1 | 12/2003 | Reggie et al. | |
| 2004/0059280 A1 | 3/2004 | Makower et al. | |
| 2004/0087887 A1 | 5/2004 | Nilsson | |
| 2004/0236309 A1 | 11/2004 | Yang | |
| 2004/0254517 A1 * | 12/2004 | Quiroz-Mercado et al. | 604/8 |
| 2005/0137646 A1 | 6/2005 | Wallace et al. | |
| 2005/0245906 A1 | 11/2005 | Makower et al. | |
| 2005/0256510 A1 | 11/2005 | Moskowitz et al. | |
| 2006/0004368 A1 * | 1/2006 | Zaleski et al. | 606/75 |
| 2006/0015152 A1 | 1/2006 | Wallace | |
| 2006/0173440 A1 | 8/2006 | Lamson et al. | |
| 2006/0224101 A1 | 10/2006 | Glenn | |
| 2007/0112291 A1 | 5/2007 | Borgesen | |
| 2007/0156218 A1 * | 7/2007 | Williams | 607/131 |
| 2007/0179426 A1 | 8/2007 | Selden | |
| 2007/0179428 A1 | 8/2007 | Kralick et al. | |
| 2007/0276316 A1 | 11/2007 | Haffner et al. | |
| 2008/0057106 A1 * | 3/2008 | Erickson et al. | 424/427 |
| 2008/0058759 A1 | 3/2008 | Makower et al. | |
| 2008/0125805 A1 | 5/2008 | Mische | |
| 2008/0249458 A1 | 10/2008 | Yamasaki | |
| 2009/0005645 A1 * | 1/2009 | Frassica et al. | 600/137 |
| 2009/0017098 A1 | 1/2009 | Di Bartolomeo | |
| 2009/0076357 A1 | 3/2009 | Purdy | |
| 2010/0076404 A1 * | 3/2010 | Ring | 604/523 |
| 2010/0121357 A1 | 5/2010 | Flaherty et al. | |
| 2010/0191168 A1 | 7/2010 | Heilman | |
| 2010/0222732 A1 | 9/2010 | Sevrain | |
| 2011/0082385 A1 * | 4/2011 | Diaz et al. | 600/558 |
| 2012/0130467 A1 | 5/2012 | Selden et al. | |
| 2014/0180098 A1 | 6/2014 | Flaherty et al. | |
| 2014/0180222 A1 | 6/2014 | Flaherty et al. | |
| 2014/0236207 A1 | 8/2014 | Makower et al. | |
| 2014/0288414 A1 | 9/2014 | Makower et al. | |

FOREIGN PATENT DOCUMENTS

| | | |
|---|---|---|
| EP | 1067869 | 1/2001 |
| EP | 1067874 | 1/2001 |
| EP | 1082070 | 3/2001 |
| EP | 1171183 | 1/2002 |
| EP | 1253859 | 11/2002 |
| EP | 1359967 | 11/2003 |
| EP | 1377335 | 1/2004 |
| EP | 1496956 | 1/2005 |
| WO | 98/16161 | 4/1998 |
| WO | 2013/034602 | 3/2013 |

OTHER PUBLICATIONS

Final Office Action for U.S. Appl. No. 12/362,152, mailed on Mar. 8, 2012 (11 pages).

Non-Final Office Action for U.S. Appl. No. 12/362,152, mailed on Aug. 5, 2011 (10 pages).

* cited by examiner

ENDOVASCULAR CEREBROSPINAL FLUID SHUNT

CROSS-REFERENCE TO RELATED APPLICATIONS

This application is a continuation of U.S. patent application Ser. No. 13/569,212 filed on Aug. 8, 2012, which is a divisional of U.S. patent application Ser. No. 12/362,152 filed on Jan. 29, 2009, the contents of which are incorporated herein by reference in its entirety.

BACKGROUND OF THE INVENTION

1. Field of the Invention

The present invention relates to an endovascular shunt implantable into the wall of a patient's sigmoid sinus, and more particularly, to a shunt capable of draining cerebrospinal fluid from the patient's subarachnoid space to the venous system.

2. Description of the Related Art

It is known to treat hydrocephalus by draining cerebrospinal fluid (CFS) from the brain with a drain tube, catheter or shunt. See U.S. Pat. Nos. 5,385,541 and 4,950,232. These known devices are complex and invasive. The risk for infection is also increased due to the complexity of these devices.

The known shunts are limited to areas of placement due to fluid flow control. Moreover, the known shunts and methods of placements do not work in conjunction with a body's natural disease control processes. Accordingly, in recent years exploration of placement of a catheter or shunt in the venous sinus of a patient has been explored. See U.S. Pat. No. 6,283,934 and Published Application No. 2005/0256510.

However, fluid flow still poses difficulties due to the complexity of the devices and the placement areas. Commonly, the shunts/catheters are placed through the skull of the patient requiring pressure control to facilitate CSF flow and also creating a dangerous infection site.

Thus, there is a need for an endovascular shunt that can be inserted into the venous system percutaneously.

SUMMARY OF THE INVENTION

The present invention relates to an endovascular CSF shunt that drains CSF from the cistern around the cerebellum into the sigmoid sinus lumen.

The present invention also relates to a method of draining CSF by inserting, deploying and detaching the shunt of the present invention by an endovascular route through the venous system. The venous system is accessed either through the femoral vein or the jugular vein percutaneously.

The endovascular cerebrospinal fluid shunt of the present invention is an improvement over the standard cerebrospinal fluid shunts because it can be placed into a patient percutaneously via a catheter inserted into the venous system of the body through a needle hole, without the need for open surgery and the skin incisions required with current shunt devices. In some patients, the device can be inserted without general anesthesia, which is not possible with current cerebrospinal fluid shunts. The device also will allow for more physiologic drainage of cerebrospinal fluid since the device is shunting cerebrospinal fluid into the same cerebral venous system that occurs naturally in normal people.

One aspect of the present invention is to provide an implantable shunt device for draining fluid from a patient's subarachnoid space. The device includes a shunt having opposed first and second ends. A one-way valve is located at the first end of the shunt and a helical tip is disposed at the second end. The helical tip penetrates the sigmoid sinus wall of the patient and a hollow passageway extending between the helical tip and the CSF cistern allows the CSF to be drained through the helical tip and out through the valve.

Another aspect of the present invention provides a method for draining cerebrospinal fluid from a patient's subarachnoid space, the method includes the steps of providing a shunt having opposed first and second ends, delivering the shunt to the sinus wall, implanting the helical tip in the sinus wall of the patient; and draining cerebrospinal fluid from the patient.

These and other features, aspects, and advantages of the present invention will become more apparent from the following detailed description of the preferred embodiment relative to the accompanied drawings, in which:

DETAILED DESCRIPTION OF THE PREFERRED EMBODIMENT

Figure 1:
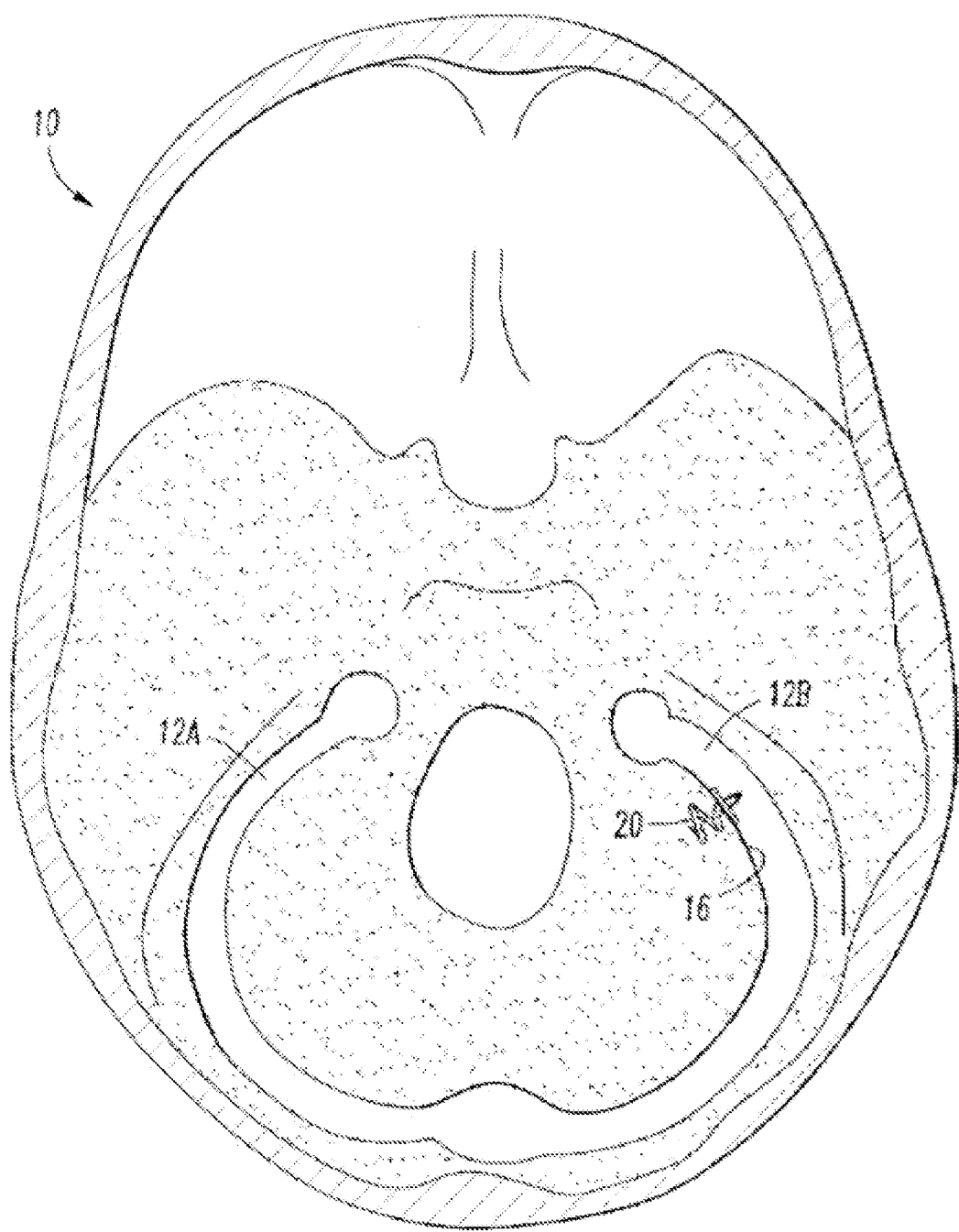
FIG. 1 is a top cross-sectional view of a human skull illustrating the placement of the shunt of the present invention.

Referring to FIG. 1, the endovascular shunt device of the present invention can be delivered to the right or left sigmoid sinus 12A, 12B of a patient's skull 10 via either the right or left jugular vein respectively of the venous system. The sigmoid sinus lumen 12 is located between the temporal bone (FIGS. 3-5) and the cerebellum.

A shunt 20 is implanted into a sigmoid sinus wall 16, so that one end communicates with CSF located in the cistern or CSF space 18 around the cerebellum 19. The device of the present invention uses the body's natural disease control mechanisms by delivering the CSF from cistern 18 into sigmoid sinus lumen 12 of the venous system. The venous system of the patient can be accesses either through the femoral or jugular veins (not shown) percutaneously. It should be appreciated that the shunt device of the present invention can be delivered to the sigmoid sinus via other locations.

Figure 2:
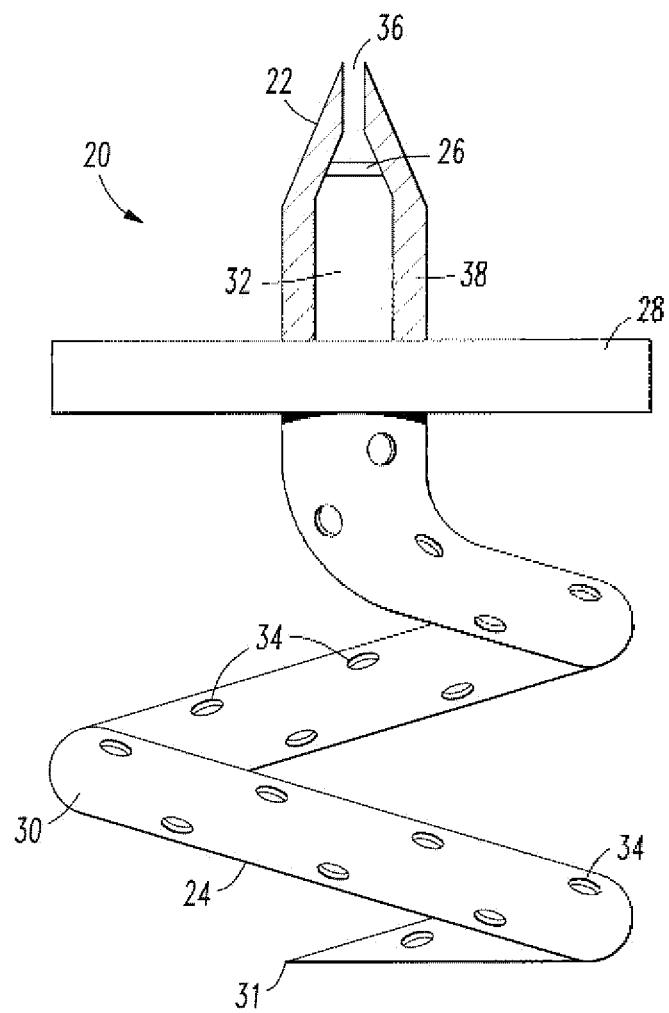
FIG. 2 is a partial cross-section of an embodiment of the endovascular shunt of the present invention.

As shown in FIG. 2, one embodiment of the endovascular CSF shunt 20 of the present invention includes opposed first and second ends 22, 24. A one-way valve 26 is located at first end 22. As will be described further herein, CSF can travel through shunt 20 and out end 22, however, other fluid cannot enter the shunt from open end 22.

A helical tip 30 is located at second end 24. As will be described further herein, helical tip 30 has a closed sharpened end 31 that is adapted to penetrate sinus wall 16. Tip 30 includes a plurality of apertures 34 through which the CSF enters the tip. A hollow passageway 32 extends from tip 30 and open end 22, such that the CSF fluid entering through apertures 34 can pass through valve 26 and pass from an outlet 36.

Figure 3:
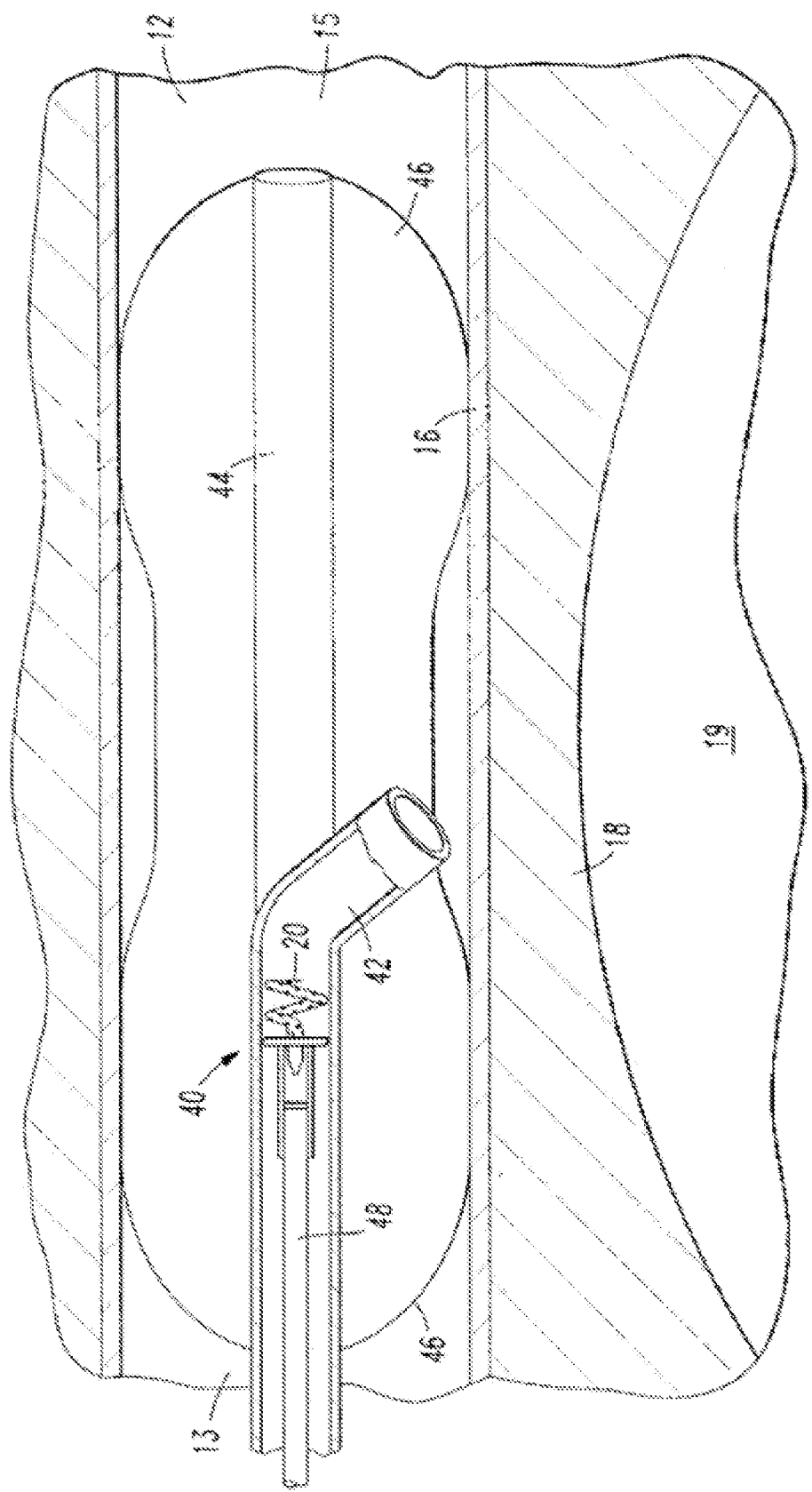
FIG. 3 is a partial view of delivering the endovascular shunt of the present invention to the CSF space of a patient's venous system.
Figure 4:
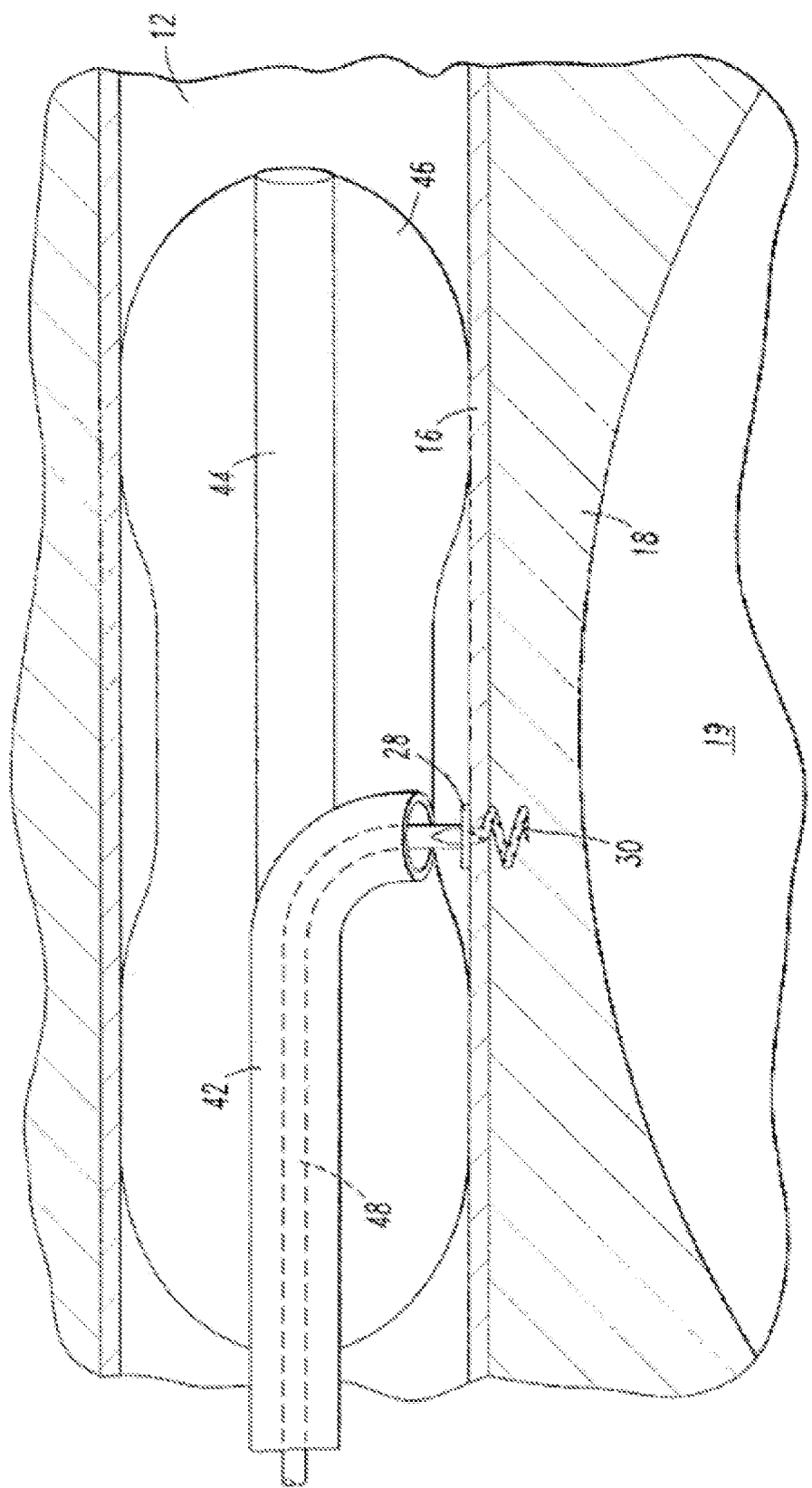
FIG. 4 is a partial view of the implantation of the endovascular shunt of the present invention into the sigmoid sinus wall.
Figure 5:
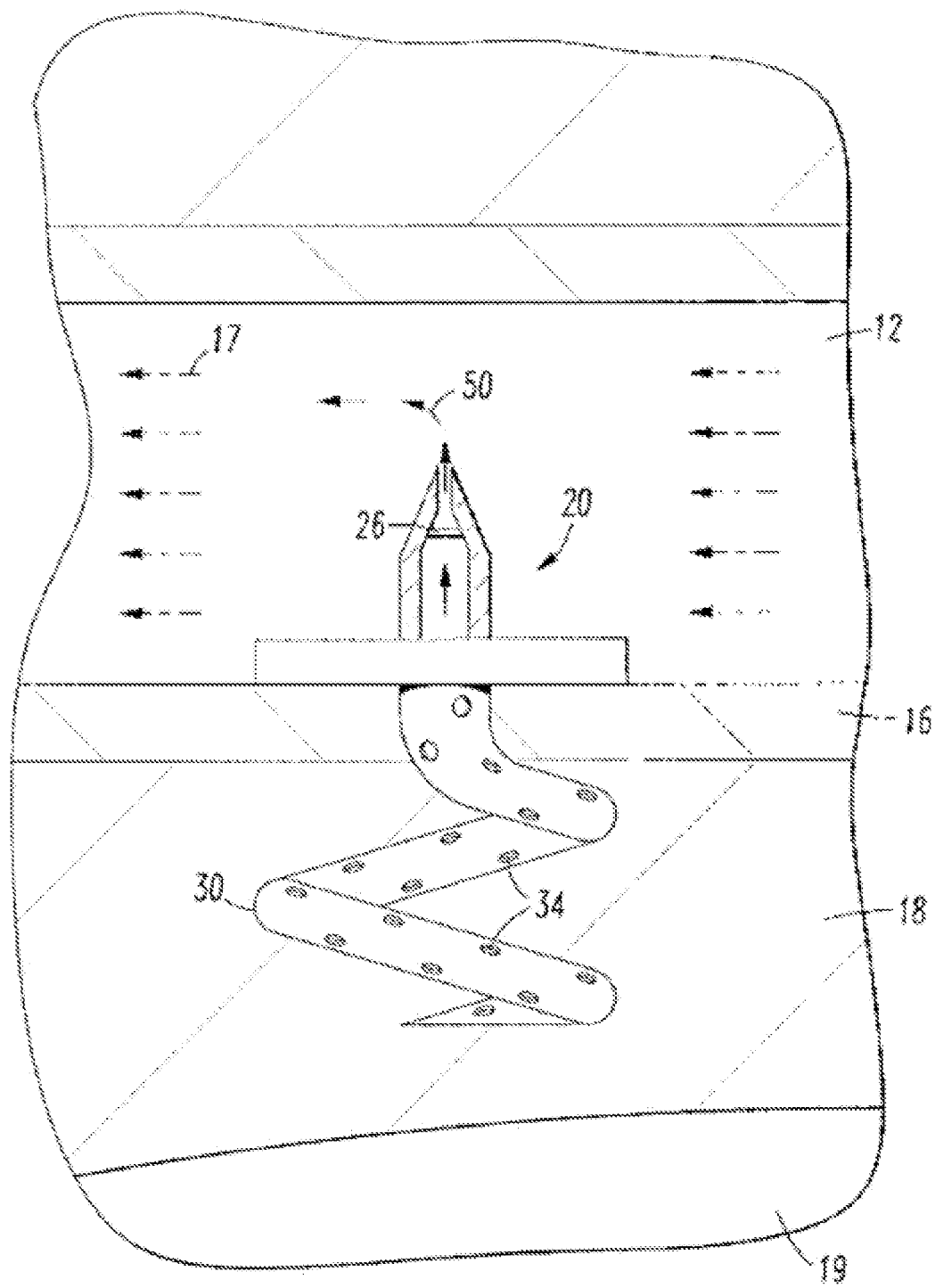
FIG. 5 is a partial view of the endovascular shunt of the present invention implanted in the sigmoid sinus wall.

Referring to FIGS. 3-5 and as described above, a delivery catheter 40 is delivered to the venous system via the femoral or jugular vein. Catheter 40 is inserted into sigmoid sinus lumen 12 at a proximal location 13 toward the neck and inserted toward a distal end 15, which is toward the brain.

Delivery catheter 40 includes a second lumen 44 and a shunt delivery port 42. Lumen 44 directs the entire catheter to the correct location with for example, a guide wire, to allow injection of intravenous contrast to visualize the venous lumen. Lumen 44 also supports balloons 46 that can be deployed to occlude venous flow during stunt implantation. Shunt 20 is positioned at an end of an internal catheter 48 that is manipulated through catheter 40 and port 42. To prevent thrombosis within the sigmoid sinus and around the endovascular shunt, shunt 20 can be provided with an antithrombic coating 38

As shown in FIG. 4, internal catheter 48 facilitates twisting of shunt 20 so that it penetrates through sigmoid sinus wall 12. Catheter 48 includes a hollow lumen to allow CSF withdrawal after shunt penetration of the sigmoid sinus wall to confirm that CSF is flowing through the shunt. However, it must be rigid enough to allow twisting of the shunt such that it penetrates the sigmoid sinus wall. Upon insertion, helical tip 30 extends into cistern 18 and CSF located therein. A projection 28 located on shunt 20 between the ends abuts the wall and prevents the shunt from passing therethrough. Upon placement, internal catheter 48 is detached. The CSF can also be aspirated back prior to detachment of catheter 48.

Thereafter, delivery catheter 40 can be removed and shunt 20 is implanted as shown in FIG. 5. CSF 50 draining from outlet 36 from CSF space 18 is delivered to the venous blood flow 17 and removed. It should be appreciated that other means of fluid removal can communicate with shunt 20 to direct the CSF as desired. It also should be appreciated that shunt 20 can incorporate different tips at end 24.

Thus, the endovascular cerebrospinal fluid shunt of the present invention can be placed into a patient percutaneously via a catheter inserted into the venous system of the body through a needle hole, without the need for open surgery and the skin incisions required with current shunt devices. In some patients, the device can be inserted without general anesthesia, which is not possible with current cerebrospinal fluid shunts. The device also will allow for more physiologic drainage of cerebrospinal fluid since the device is shunting cerebrospinal fluid into the same cerebral venous system that occurs naturally in normal people.

Although the present invention has been described in relation to particular embodiments thereof, many other variations and modifications and other uses will become apparent to those skilled in the art. It is preferred therefore, that the present invention be limited not by the specific disclosure herein, but only by the appended claims.

The invention claimed is:

1. An endovascular implantable shunt device for draining cerebrospinal fluid from a patient's subarachnoid space to the venous system, the device comprising:
    a shunt having opposed first and second ends;
    a one-way valve located at the first end of the shunt;
    a helical tip disposed at the second end, said helical tip being constructed to penetrate a sinus wall of the patient; and
    a hollow passageway extending between the helical tip and one-way valve such
    that cerebrospinal fluid can be drained through the helical tip and out through the valve.

2. The shunt of claim 1, wherein the helical tip includes a plurality of apertures into which the cerebrospinal fluid enters the tip.

3. The shunt of claim 1, wherein the shunt includes an antithrombic coating.

4. The shunt of claim 1, wherein said helical tip comprises a closed sharpened end.

5. The shunt of claim 1, wherein said helical tip defines a helix having constant radius.

6. The shunt of claim 1, wherein said first end is tapered.

7. The shunt of claim 1, further comprising a projection between said first and second end, wherein said projection extends along a plane perpendicular to a line extending between said first and second ends of said shunt.

8. The shunt of claim 1, wherein said one-way valve is oriented to block liquid from flowing from said first end toward said second end and to permit liquid to flow from said second end toward said first end.

9. A system for draining cerebrospinal fluid from a patient's subarachnoid space to the venous system, the system comprising:
    an endovascular implantable shunt having opposed first and second ends, a one-way valve located at the first end of the shunt, and a helical tip disposed at the second end, said helical tip being constructed to penetrate a sinus wall of the patient, wherein the first
    and second ends are in fluid communication to enable the cerebrospinal fluid to be drained through the helical tip and out through the valve; and
    a catheter for delivering percutaneously and implanting the shunt into the sinus wall.

10. An endovascular implantable shunt device for draining fluid from a patient's subarachnoid space to the venous system, the device comprising:
    a shunt having opposed first and second ends capable of being deployed by an endovascular route through the venous system;
    a one-way valve located at the first end of the shunt; and
    a helical tip disposed at the second end, said helical tip being constructed to penetrate tissue of the patient; and
    a hollow passageway extending between the helical tip and one-way valve such that fluid can be drained through the helical tip and out through the valve.

* * * * *